United States Patent
Takasaki

(10) Patent No.: US 9,822,159 B2
(45) Date of Patent: Nov. 21, 2017

(54) ELECTROMAGNETIC BAND GAP ELEMENT, ELECTRONIC CIRCUIT, AND CONDUCTOR STRUCTURE

(71) Applicant: CANON KABUSHIKI KAISHA, Tokyo (JP)

(72) Inventor: Atsushi Takasaki, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 168 days.

(21) Appl. No.: 14/454,582

(22) Filed: Aug. 7, 2014

(65) Prior Publication Data

US 2015/0054713 A1 Feb. 26, 2015

(30) Foreign Application Priority Data

Aug. 21, 2013 (JP) ................................. 2013-171709

(51) Int. Cl.

| | |
|---|---|
| *H01Q 1/38* | (2006.01) |
| *C07K 14/705* | (2006.01) |
| *C12Q 1/68* | (2006.01) |
| *G01N 33/566* | (2006.01) |
| *A61K 38/00* | (2006.01) |

(52) U.S. Cl.
CPC .......... *C07K 14/705* (2013.01); *C12Q 1/6876* (2013.01); *G01N 33/566* (2013.01); *A61K 38/00* (2013.01); *C12Q 2600/156* (2013.01); *G01N 2500/10* (2013.01); *Y10S 435/81* (2013.01)

(58) Field of Classification Search
CPC ............ H01Q 15/008; H01Q 15/0026; H01Q 15/0006; H01Q 15/006
USPC .................................................. 343/700 MS
See application file for complete search history.

(56) References Cited

U.S. PATENT DOCUMENTS

| | | |
|---|---|---|
| 6,262,495 B1 | 7/2001 | Yablonovitch et al. |
| 6,289,036 B1 | 9/2001 | Saito et al. |
| 6,707,841 B1 | 3/2004 | Takasaki |
| 8,779,874 B2 | 7/2014 | Toyao |
| 2004/0160367 A1 | 8/2004 | Mendolia et al. |
| 2013/0314285 A1 | 11/2013 | Takasaki |

FOREIGN PATENT DOCUMENTS

| | | |
|---|---|---|
| JP | 2002-510886 A | 4/2002 |
| JP | 2010-010183 A | 1/2010 |
| JP | 2010-199881 A | 9/2010 |
| JP | 2014-233053 A | 12/2014 |

*Primary Examiner* — Graham Smith
(74) *Attorney, Agent, or Firm* — Fitzpatrick, Cella, Harper & Scinto

(57) ABSTRACT

An electromagnetic band gap element is provided. In the electromagnetic band gap element, a first planar conductor and a second planar conductor are respectively formed on a first plane and a second plane which are parallel to each other, and a first linear conductor is formed on at least one third plane that is parallel to the first plane and the second plane and is located between the first plane and the second plane. The first planar conductor and the second planar conductor are connected via the first linear conductor.

10 Claims, 10 Drawing Sheets

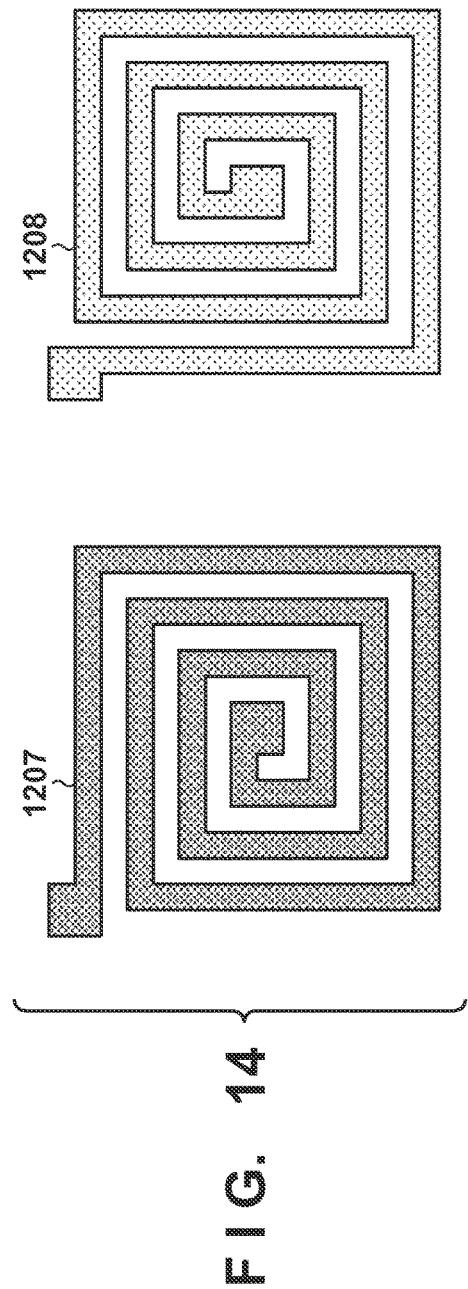
F I G. 14
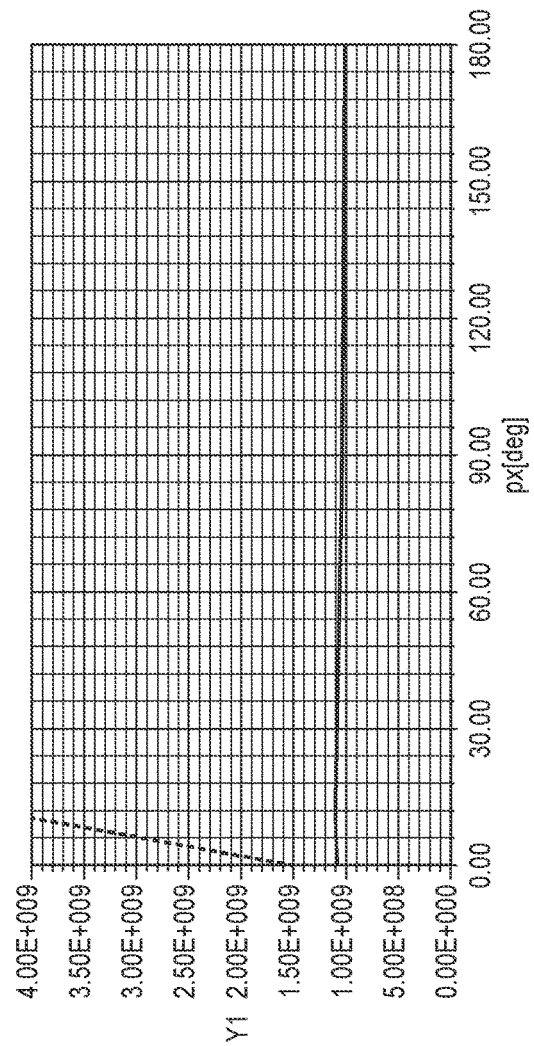
F I G. 15

ELECTROMAGNETIC BAND GAP ELEMENT, ELECTRONIC CIRCUIT, AND CONDUCTOR STRUCTURE

BACKGROUND OF THE INVENTION

Field of the Invention

The present invention relates to an element having an electromagnetic band gap (EBG) structure that prevents propagation of an electromagnetic wave in a specific frequency band.

Description of the Related Art

In recent years, an electromagnetic band gap technology for preventing propagation of an electromagnetic wave in a specific frequency band has been examined. An electromagnetic band gap structure exhibits a magnetic wall effect and can therefore be used to reduce the height of an antenna.

A general electromagnetic band gap structure is a mushroom structure in which conductor patches are arranged at a predetermined gap interval in an array pattern on the same plane, and conductive vias are connected from the conductor patches to ground conductors parallel to the conductor patches (see Japanese Patent Laid-Open No. 2002-510886). Japanese Patent Laid-Open No. 2010-010183 describes a structure of an electromagnetic band gap element including an open stub inserted between parallel plates.

The conventional mushroom type electromagnetic band gap structure is not suitable for incorporation in a compact electronic device because one cell is large. Note that according to, for example, the technique described in Japanese Patent Laid-Open No. 2010-010183, the electromagnetic band gap structure can be made small using an open stub. However, further size reduction is demanded.

The present invention has been made in consideration of the above-described problem, and reduces the size of an electromagnetic band gap structure.

SUMMARY OF THE INVENTION

According to one aspect of the present invention, there is provided an electromagnetic band gap element comprising: a first planar conductor and a second planar conductor respectively formed on a first plane and a second plane which are parallel to each other; and a first linear conductor formed on at least one third plane that is parallel to the first plane and the second plane and is located between the first plane and the second plane, wherein the first planar conductor and the second planar conductor are connected via the first linear conductor.

According to another aspect of the present invention, there is provided a conductor structure comprising: a first planar conductor and a second planar conductor respectively formed on a first plane and a second plane which are parallel to each other; and a plurality of linear conductors arranged in a dielectric region sandwiched between the first planar conductor and the second planar conductor in parallel to the first plane and the second plane, wherein the plurality of linear conductors are connected by a via, thereby forming a continuous conductor.

Further features of the present invention will become apparent from the following description of exemplary embodiments with reference to the attached drawings.

BRIEF DESCRIPTION OF THE DRAWINGS

FIG. 14 is a plan view showing an example of the arrangement of conductors formed in the surface layer and the inner layer of the electromagnetic band gap element according to the second embodiment;

FIG. 15 is a graph showing the dispersion characteristic of the unit cell of the electromagnetic band gap element according to the second embodiment;

DESCRIPTION OF THE EMBODIMENTS

Exemplary embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

<<First Embodiment>>

In this embodiment, an electromagnetic band gap element having a planar conductor patch and ground conductor arranged on two parallel planes includes linear conductors respectively formed on two planes parallel to these planes. More specifically, the conductors are formed in four layers of parallel planes. The conductor patch is arranged on the uppermost plane. The ground conductor is arranged on the lowermost plane. The linear conductors are formed on the two planes of the inner layer. One end of the linear conductor on the second plane is connected to the conductor patch by a via, and the other end is connected to one end of the linear conductor on the third plane similarly by a via. The one end of the linear conductor on the third plane is connected to the end of the linear conductor on the second plane by the via, as described above, and the other end is connected to the ground conductor by a via. That is, in this embodiment, all the conductors formed in the four layers are connected, and take a structure like the conventional mushroom structure in which the vias that connect the conductor patch and the ground conductor of the electromagnetic band gap element are deformed. This structure will be described below in detail. Note that although a term such as "linear conductor" will be used below, strictly speaking, the conductor is often formed by printing a thin conductor plate on one plane. For this reason, a conductor actually formed as a plate will also be referred to as a "linear conductor" here, including a conductor that forms one line by extending a conductor plate.

Figure 1:
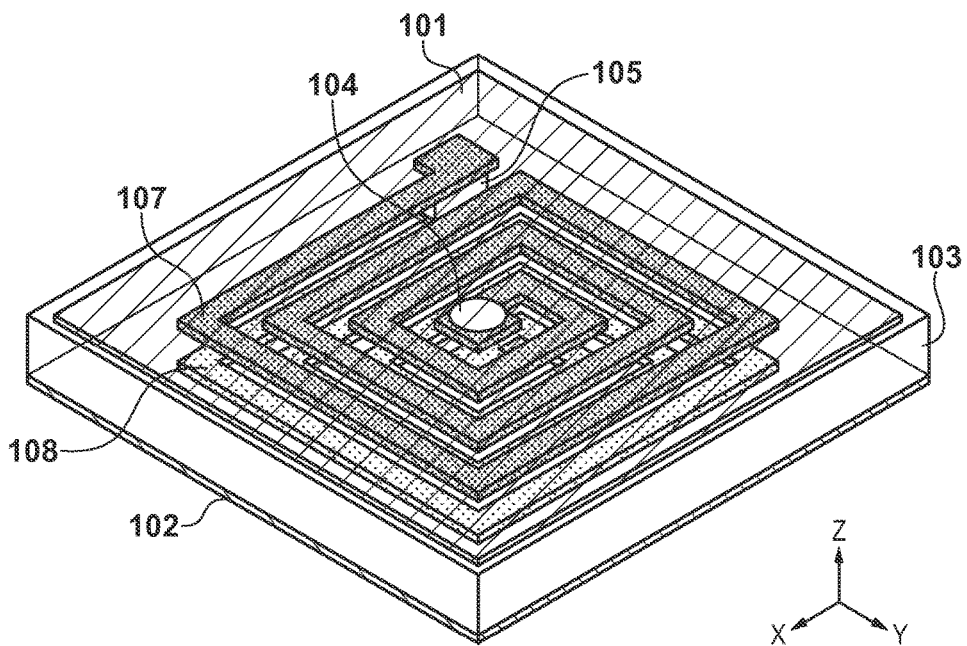
FIG. 1 is a schematic view showing the unit cell structure of an electromagnetic band gap element according to the first embodiment.
Figure 2:
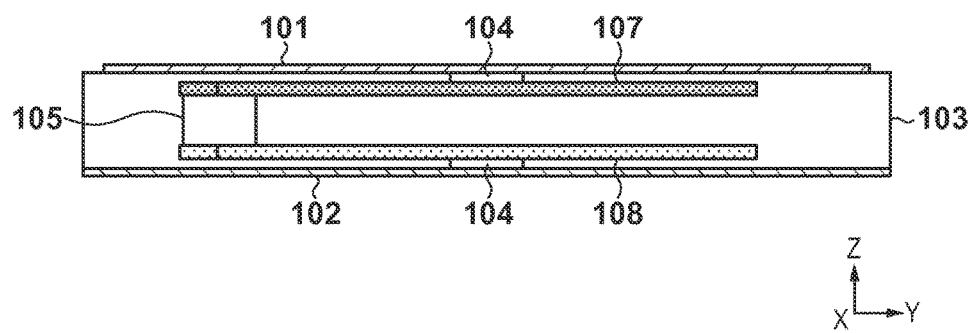
FIG. 2 is a sectional view of the unit cell structure of the electromagnetic band gap element according to the first embodiment.

FIG. 1 is a schematic view showing a state in which the unit cell structure of an electromagnetic band gap element according to this embodiment is constructed in a general 4-layer printed board. Note that FIG. 1 partially includes a perspective view so as to explain the internal conductor structure. FIG. 2 is a sectional view of the unit cell structure shown in FIG. 1 viewed from one (direction from lower left to upper right in FIG. 1) of X-axis directions (directions perpendicular to the Y-Z plane).

The electromagnetic band gap element shown in FIGS. 1 and 2 includes a conductor patch 101 and a ground conductor 102 of the surface layers, a dielectric 103 that fills the space between the conductor patch 101 and the ground conductor 102, vias 104 to 106, and spiral conductors 107 and 108 of the inner layer. The conductor patch 101 of the surface layer is connected to the first spiral conductor 107 of the inner layer by the via 104. The ground conductor 102 of the lowermost layer is connected to the second spiral conductor 108 of the inner layer by the via 106. The first spiral conductor 107 and the second spiral conductor 108 of the inner layer are connected to each other by the via 105. In this structure, a plurality of (two, in this case) linear conductors are arranged in a dielectric region sandwiched between a first plane on which the conductor patch 101 is formed and a second plane on which the ground conductor 102 is formed so as to be parallel to the first plane and the second plane. The plurality of linear conductors are connected at ends by a via, and have a continuous conductor structure.

Figure 3:
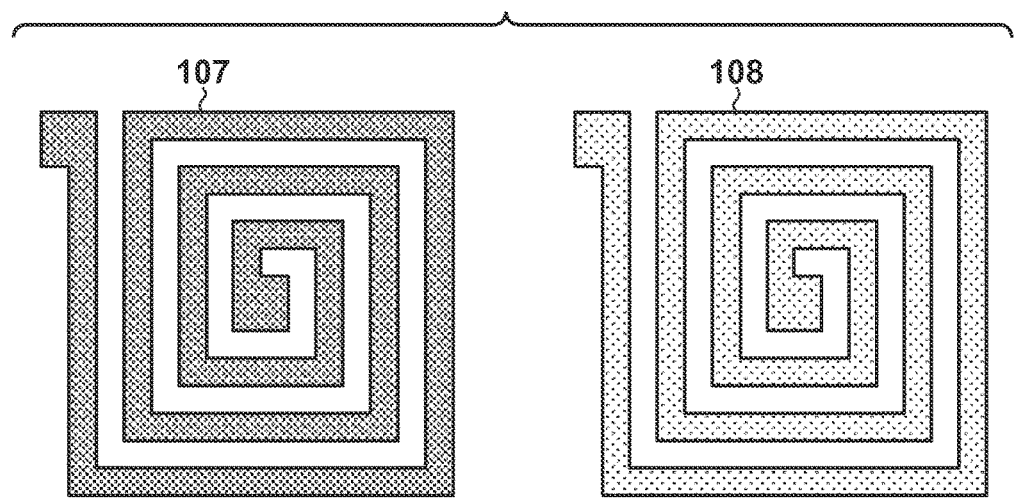
FIG. 3 is a plan view showing an example of the arrangement of conductors formed in the inner layer of the electromagnetic band gap element according to the first embodiment.

FIG. 3 is a plan view showing the spiral conductors 107 and 108 of the inner layer. Note that FIG. 3 shows the spiral conductors 107 and 108 viewed from the upper surface side (direction perpendicular to the X-Y plane in which the second spiral conductor 108 can be seen on the far side of the first spiral conductor 107) in FIG. 1. The two spiral conductors 107 and 108 have spiral shapes in the same winding direction, and are connected by the via 105 at the ends (upper left ends in FIG. 3) on the outer side of the spirals. The ends at the center of the spiral shapes are connected to the conductors of the surface layer and the ground layer by the vias 104 and 106, respectively.

Figure 4:
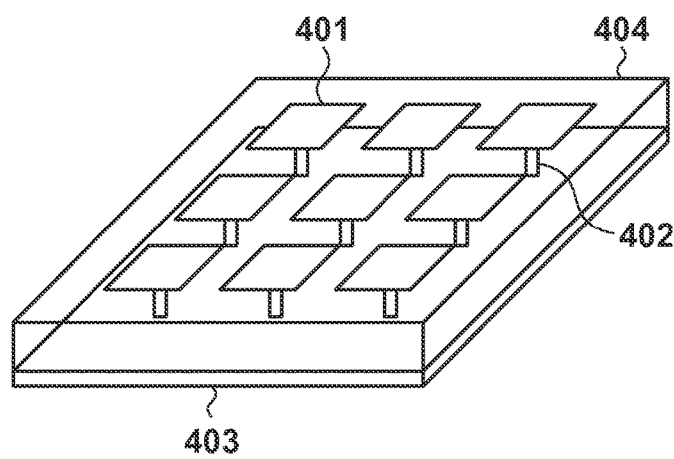
FIG. 4 is a schematic view showing a general electromagnetic band gap structure.

To explain an effect given by an increase in the reactance component of the spiral structure according to this embodiment, the operation of a general EBG (Electromagnetic Band Gap) element will be described next. FIG. 4 is a perspective view showing an example of a general EBG structure. In general, the EBG structure is formed from conductor patches 401, conductive vias 402, a ground conductor 403 on the lower surface, and a dielectric 404. Note that an air space may replace the dielectric 404. The conductive via 402 is configured to penetrate the dielectric 404 and electrically connect the conductor patch 401 and the ground conductor 403 on the lower surface.

Figure 5:
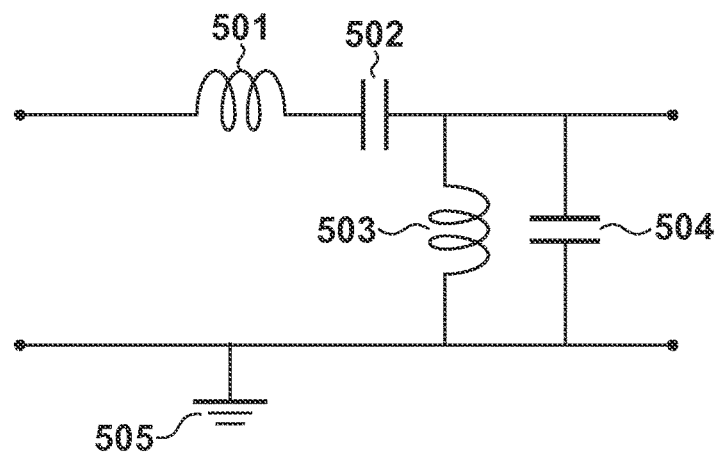
FIG. 5 is an equivalent circuit diagram of the unit cell of the general electromagnetic band gap structure.

FIG. 4 shows a cell structure having a two-dimensional array of 3×3 cells. Focusing a unit cell (one cell) for the descriptive simplicity, the equivalent circuit of the unit cell can be expressed as in FIG. 5.

A series inductive reactance 501 corresponds to the length of the conductor patch 401 in a direction parallel to the ground conductor 403. A series capacitive reactance 502 corresponds to the gap between the adjacent conductor patches periodically arrayed. On the other hand, a parallel inductive reactance 503 corresponds to the conductive via 402 that electrically connects the conductor patch 401 and the ground conductor 403. A capacitive reactance 504 connected in parallel between a signal line and the ground corresponds to the gap between the conductor patch 401 and the ground conductor 403. Ground 505 corresponds to the ground conductor 403.

The phase constant is 0 in the frequency band between the resonance frequency of the series resonance circuit formed from the series elements 501 and 502 and the resonance frequency of the parallel resonance circuit formed from the parallel elements 503 and 504. This frequency band is the band gap that does not pass an electromagnetic wave. Hence, the circuit can be designed so as to obtain a band gap characteristic in a desired frequency band by adjusting the series resonance frequency and the parallel resonance frequency. In the EBG structure shown in FIG. 4, a structure that blocks an electromagnetic wave in a desired frequency band can be formed by adjusting parameters such as the size of a conductor patch, the interval between adjacent patches, and the diameter and length of a via.

An equivalent circuit concerning the unit cell structure of the electromagnetic band gap element shown in FIGS. 1 and 2 will be considered here. In the circuit according to this embodiment, the via 104, the spiral conductor 107 of the inner layer, the via 105, the spiral conductor 108 of the inner layer, and the via 106 are sequentially connected in series. For this reason, all the elements correspond to the parallel element 503 in FIG. 5. The reactance component of the linear conductor increases in accordance with its length. In the parallel resonance circuit, when the reactance component increases, an effect of lowering the resonance frequency can be obtained.

In the general EBG structure shown in FIG. 4, to increase the reactance component of the parallel resonance circuit, for example, the board thickness needs to increase. This affects other design parameters and causes, for example, a decrease in the capacitive component of the conductor patch of the surface layer. On the other hand, according to the structure of this embodiment, the reactance component of the parallel resonance circuit can be increased only by extending the path length as the conductor almost without any influence on the other design dimensions such as the board thickness and the dimensions of the conductor patch of the surface layer. It is therefore possible to implement a lower resonance frequency under the same dimensional conditions as compared to the general EBG structure and increase the degree of freedom in the band gap design. In addition, it is possible to reduce the dimensions needed by the structure according to this embodiment to implement the same reactance component as in the conventional structure. That is, the electromagnetic band gap element can be made compact.

Figure 6:
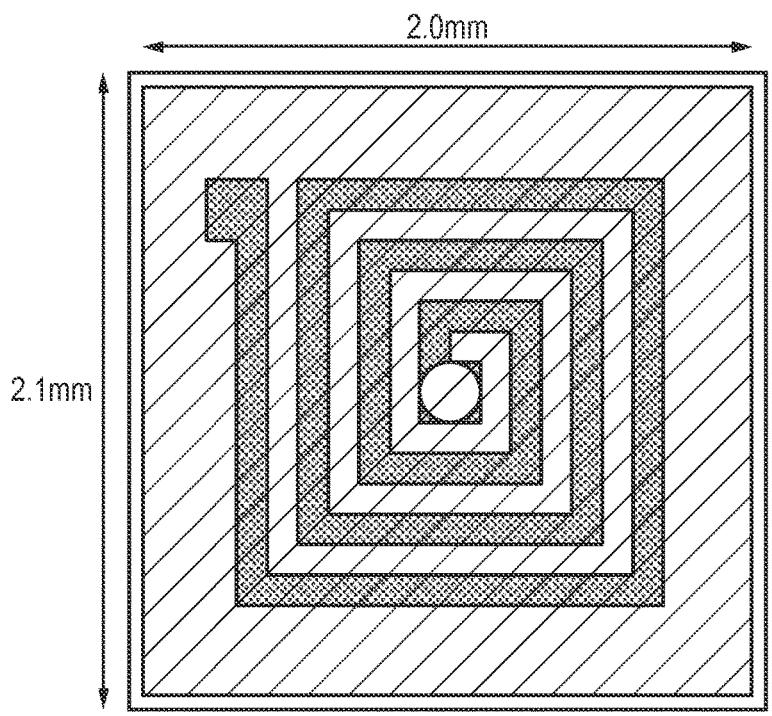
FIG. 6 is a view showing an example of the dimensions of the electromagnetic band gap element.

Circuit calculation and analysis were conducted for the electromagnetic band gap element according to this embodiment. FIG. 6 shows the outline of dimensions used in the circuit calculation and analysis. As shown in FIG. 6, in the following circuit calculation and analysis, the unit cell size was set to 2.1 mm×2.1 mm, and the size of the conductor patch 101 of the surface layer was set to 2.0 mm×2.0 mm. An FR-4 board having a 4-layer structure was used in which standard numerical values were used as the board thickness, the distances between the layers, and the like, and a description thereof will be omitted here.

Figure 7:
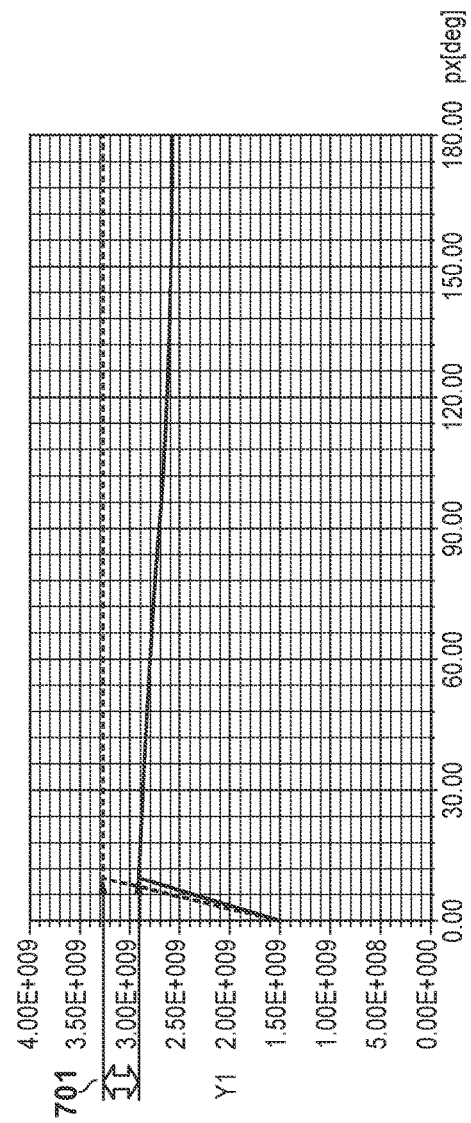
FIG. 7 is a graph showing the dispersion characteristic of the unit cell of the electromagnetic band gap element according to the first embodiment.
Figure 8:
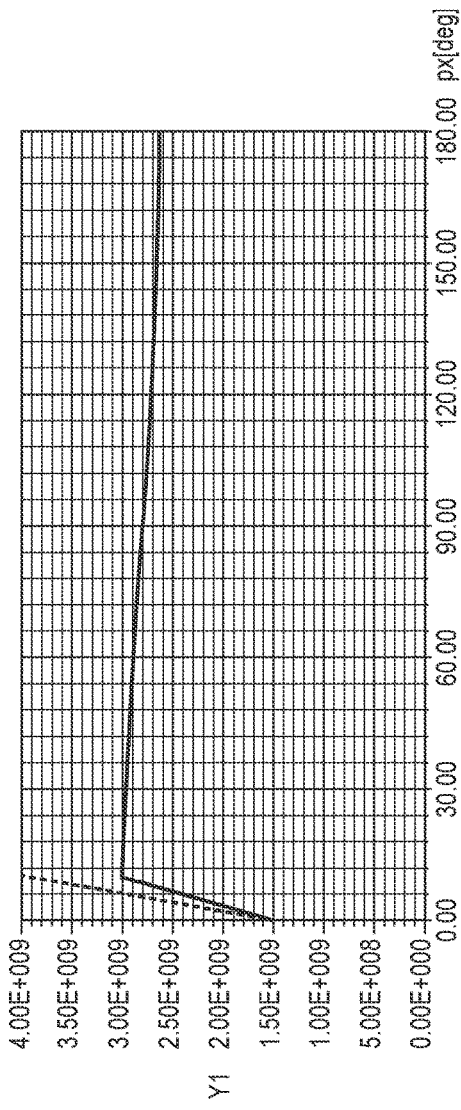
FIG. 8 is a graph showing the dispersion characteristic of the unit cell of the electromagnetic band gap element including one layer of a spiral structure.
Figure 9:
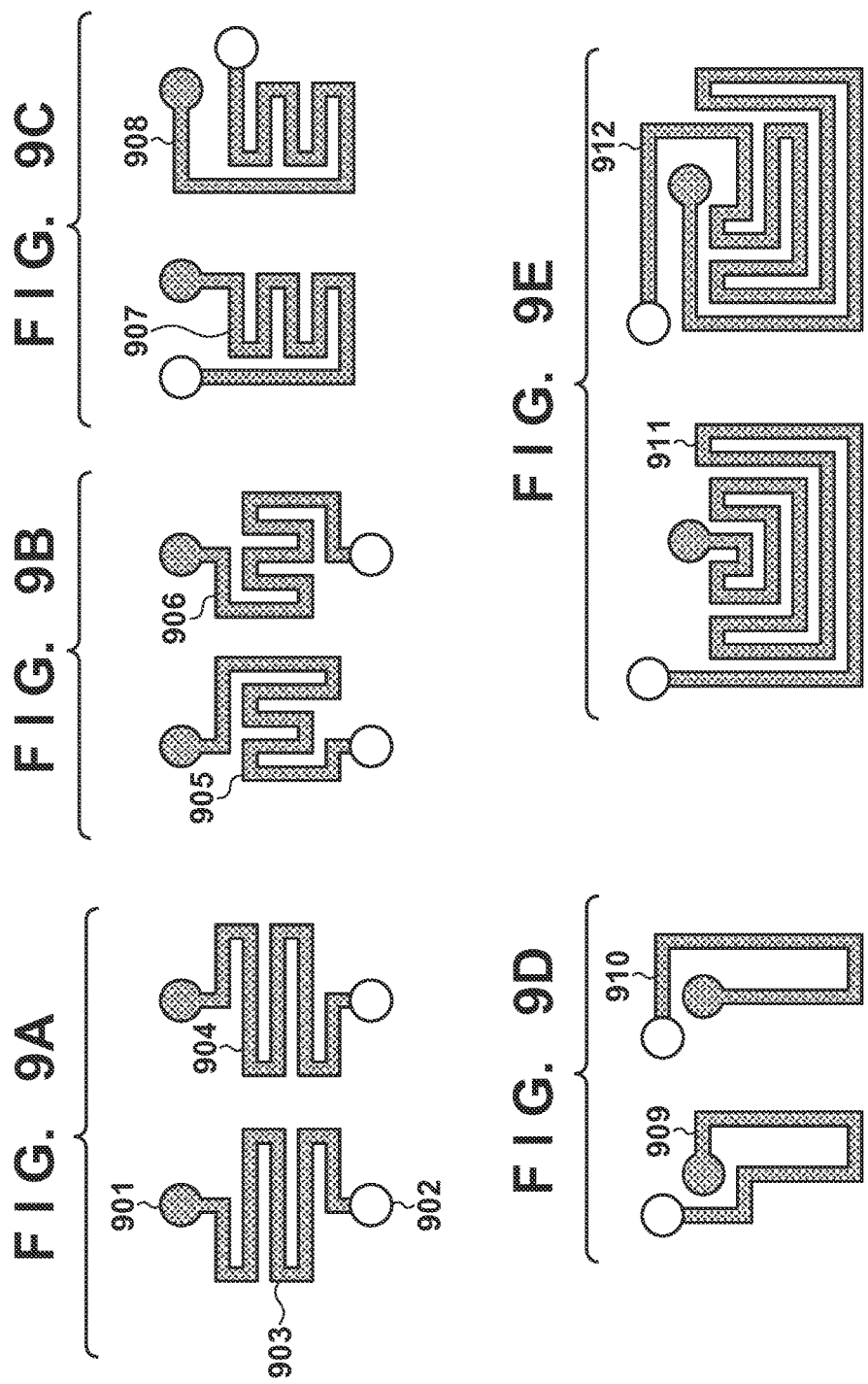
FIGS. 9A to 9E are views showing examples of the arrangement of conductor patterns of the inner layer according to the first embodiment.

FIG. 7 is a graph showing the dispersion characteristic of the unit cell of the electromagnetic band gap element according to this embodiment. As is apparent from FIG. 7, the electromagnetic band gap element according to this embodiment has a band gap characteristic 701 representing that the phase constant is 0 within the range of a frequency band from about 2.9 GHz to 3.3 GHz. For the sake of comparison, FIG. 8 shows the dispersion characteristic in a case where the electromagnetic band gap element includes only one layer of a spiral structure in the inner layer. The dispersion characteristic of the electromagnetic band gap element according to this embodiment shown in FIG. 7 can lower the frequency by about 100 MHz as compared to the characteristic shown in FIG. 8 in the case where there exists only one layer of a spiral structure, as can be seen. That is, when the spiral structures are formed in two or more layers, the reactance component can effectively be increased, as is apparent. Note that even if there is only one layer of a spiral structure, the path length extending effect can be obtained, and the frequency can therefore be lowered as compared to the conventional electromagnetic band gap element.

Note that in this embodiment, two conductors having the same spiral shape are used. However, the band gap frequency can be lowered by extending the path length using a multilayered structure and thus increasing the reactance component. FIGS. 9A to 9E illustrate examples of conductor patterns configured to extend the path length. Referring to FIGS. 9A to 9E, for example, a fill circle 901 represents a terminal on the side where ends of the linear conductors are connected by a via, and an open circle 902 represents a terminal at which the linear conductor is connected to the conductor patch of the surface layer or the ground conductor of the lowermost layer. Conductors 903 and 904 in FIG. 9A, conductors 905 and 906 in FIG. 9B, conductors 907 and 908 in FIG. 9C, conductors 909 and 910 in FIG. 9D, and conductors 911 and 912 in FIG. 9E have paired shapes. However, for the purpose of extending the path length, any combination is usable as long as it is configured to connect the terminals to each other. Alternatively, a multilayered structure including three or more layers may be formed to connect the terminals.

In the above-described arrangement, the spiral conductors 107 and 108 of the inner layer have spiral shapes in the same winding direction. However, the present invention is not limited to this. For example, as shown in FIG. 10, a first spiral conductor 1001 and a second spiral conductor 1002 may have spiral shapes in opposite winding directions.

Note that in this case as well, the first spiral conductor 1001 is connected to the conductor patch 101 by the via 104 at the endpoint inside the spiral, and also connected to the second spiral conductor 1002 by the via 105 at the endpoint outside the spiral, as shown in FIG. 2. Similarly, the second spiral conductor 1002 is connected to the first spiral conductor 1001 by the via 105 at the endpoint outside the spiral, and also connected to the ground conductor 102 by the via 106 at the endpoint inside the spiral.

With this arrangement, when the conductive path from the conductor patch 101 of the surface layer is traced, the center of the conductor patch 101 is connected to the first spiral conductor 1001 by the via 104. In the first layer, the conductive path is formed counterclockwise from the center to the outer end. After that, the end on the outer side is connected to the second spiral conductor 1002 by the via 105. In the second layer, the conductive path is formed also counterclockwise from outer end of the spiral to the center. As a result, currents basically flow in the same direction at portions of the two spiral shapes which overlap when viewed from a direction perpendicular to the planes where the linear conductors are formed, and magnetic fields formed by the currents also have the same direction. For this reason, the magnetic fields have the effect of enhancing each other, and the reactance component is efficiently increased. Note that the currents need not have the same direction in all or almost all portions, as in the spiral shapes described here. The linear conductors may be formed in the layers such that the currents have the same direction in part.

Figure 10:
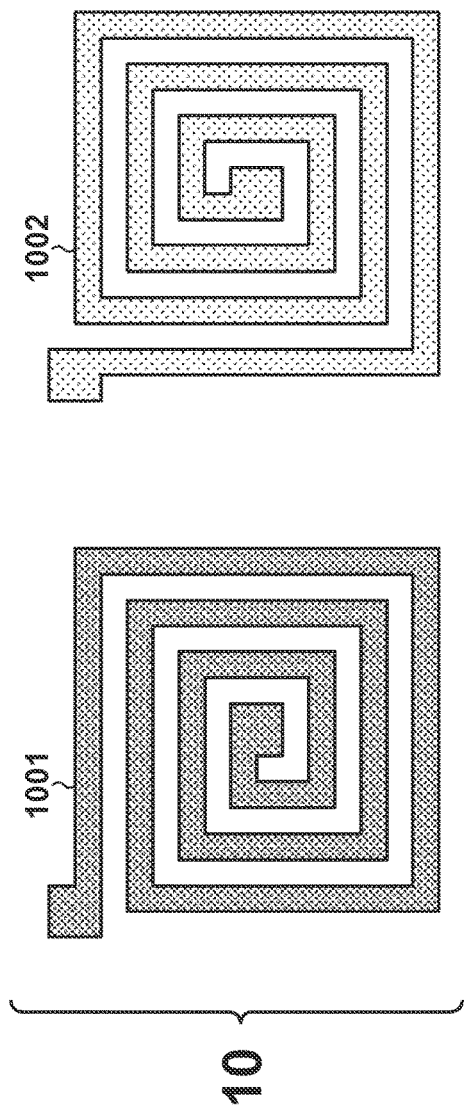
FIG. 10 is a plan view showing another example of the arrangement of the conductors formed in the inner layer of the electromagnetic band gap element according to the first embodiment.
Figure 11:
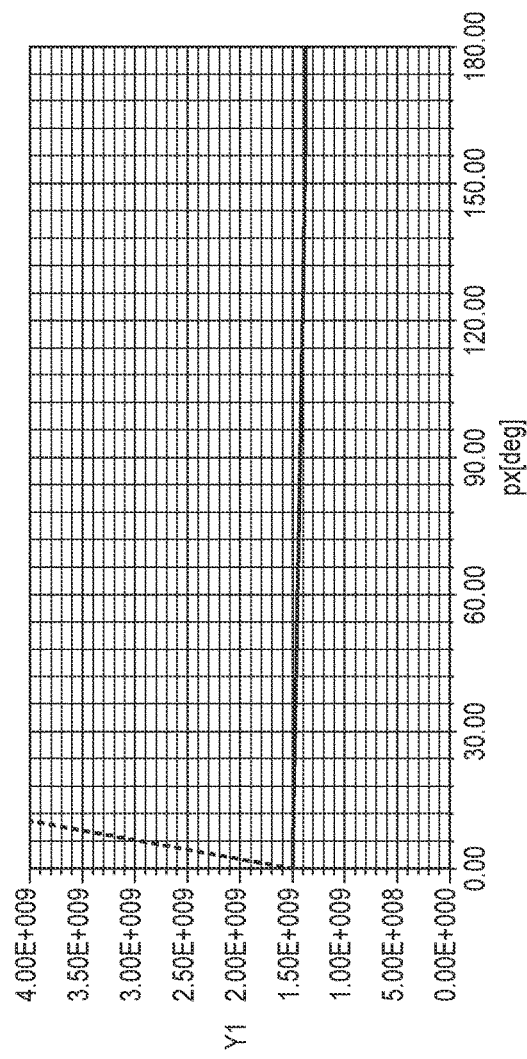
FIG. 11 is a graph showing the dispersion characteristic of the unit cell of an electromagnetic band gap element having the conductor arrangement shown in FIG. 10 in the inner layer.

FIG. 11 shows the dispersion characteristic of the unit cell of an electromagnetic band gap element including conductors having the shapes shown in FIG. 10. As is apparent from FIG. 11, this structure has a band gap characteristic representing that the phase constant is 0 in a frequency band of 1.5 GHz or more. This structure can more efficiently increase the reactance component and lower the band gap frequency as compared to a case where an electromagnetic band gap element having the conductors shown in FIG. 3 is used.

In this example, two spiral conductors are used. However, the present invention is not limited to this. For example, when the path length is extended using a multilayered structure including two or more layers, and the conductor shapes are determined such that the currents at the overlapping conductor portions have the same direction as much as possible, the reactance component can more efficiently be increased. As the arrangement of the linear conductors, conductor arrangements of various shapes as shown in FIGS. 9A to 9E are usable. For example, the conductors 903 and 904 in FIG. 9A, the conductors 905 and 906 in FIG. 9B, the conductors 907 and 908 in FIG. 9C, the conductors 909 and 910 in FIG. 9D, and the conductors 911 and 912 in FIG. 9E have paired shapes that set the currents flowing through the main conductor portions in phase in terms of high frequencies when the conductors overlap in a multilayered structure. For this reason, use of these conductors can also be expected to effectively increase the reactance component. Even when conductors having these shapes are formed into a multilayered shape including three or more layers, the same effect can be maintained by alternately repetitively overlaying the combined shapes.

<<Second Embodiment>>

In the first embodiment, the arrangement of an electromagnetic band gap element has been described which increases the reactance component by forming a conductor patch and a ground conductor on two planes, forming linear conductors on two planes between them, and thus connecting the conductor patch and the ground conductor. In the second embodiment, the arrangement of an electromagnetic band gap element will be described which increases the reactance component by forming one linear conductor on the same plane as a conductor patch and forming a linear conductor on one plane between the conductor patch and a ground conductor.

Figure 12:
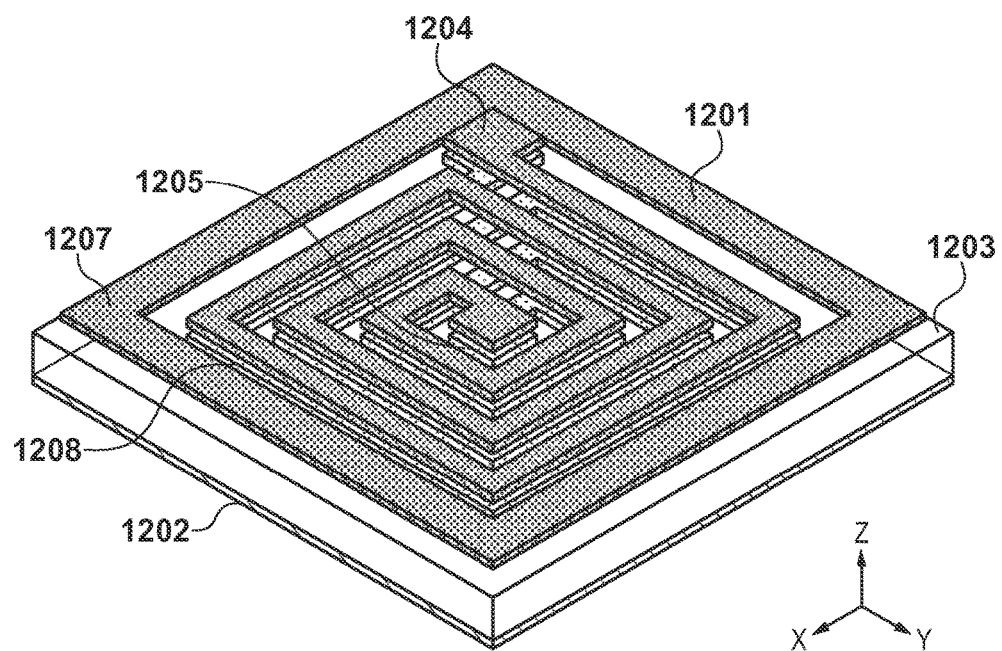
FIG. 12 is a schematic view showing the unit cell structure of an electromagnetic band gap element according to the second embodiment.
Figure 13:
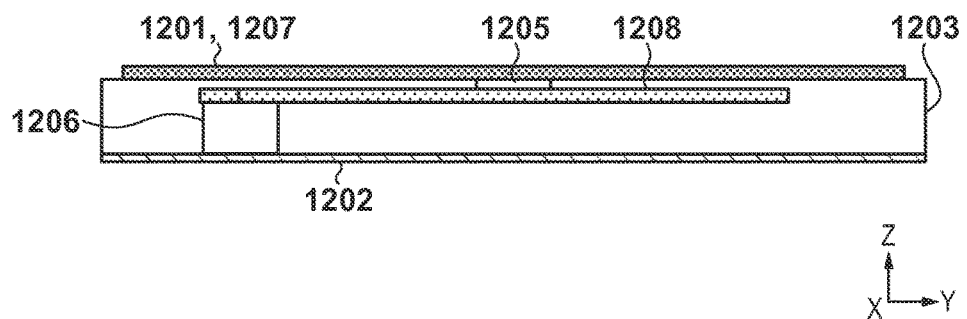
FIG. 13 is a sectional view of the unit cell structure of the electromagnetic band gap element according to the second embodiment.

FIG. 12 is a schematic view showing a state in which the unit cell structure of an electromagnetic band gap element according to this embodiment is constructed in a general 3-layer printed board. Note that FIG. 12 partially includes a perspective view so as to explain the internal conductor structure. FIG. 13 is a sectional view of the unit cell structure shown in FIG. 12 viewed from one (direction from lower left to upper right in FIG. 12) of X-axis directions (directions perpendicular to the Y-Z plane). As shown in FIG. 12, in the electromagnetic band gap element according to this embodiment, the central portion of the planar conductor of the conductor patch is hollowed out, and a linear conductor having a spiral shape is formed in the hollow portion. That is, in this embodiment as well, the linear conductors are formed on two planes, and one of the linear conductors is formed on the same plane as the conductor patch. Note that although the linear conductor is formed on the same plane as the conductor patch in this embodiment, the linear conductor may be formed on the plane where the ground conductor is formed.

The electromagnetic band gap element shown in FIGS. 12 and 13 includes a conductor patch 1201 and a spiral conductor 1207 on the upper surface of the board of a dielectric 1203, a ground conductor 1202 on the lower surface of the board of the dielectric 1203, and a spiral conductor 1208 of the inner layer between the two planes. An endpoint of the first spiral conductor 1207 is connected to the conductor patch 1201 at a node 1204, and the other endpoint is connected to one endpoint of the second spiral conductor 1208 by a via 1205. The one endpoint of the second spiral conductor 1208 is connected to the first spiral conductor 1207 by the via 1205, as described above, and the other endpoint is connected to the ground conductor 1202 by a via 1206. Hence, the conductor patch 1201 and the ground conductor 1202 form a continuous conductor through the spiral conductors 1207 and 1208, the vias 1205 and 1206, and the node 1204.

In the electromagnetic band gap element according to this embodiment, one (first spiral conductor 1207) of the spiral conductors is formed on the same plane as the plane where the conductor patch 1201 is formed, and for example, surrounded by the conductor patch, as shown in FIG. 12.

FIG. 14 is a plan view showing the first spiral conductor 1207 formed on the surface layer and the second spiral conductor 1208 formed in the inner layer. FIG. 14 shows the spiral conductors 1207 and 1208 viewed from the upper surface side (direction perpendicular to the X-Y plane in which the second spiral conductor 1208 can be seen on the far side of the first spiral conductor 1207) in FIG. 12. The two spiral conductors 1207 and 1208 have spiral shapes winding in directions opposite to each other. More specifically, the first spiral conductor 1207 winds clockwise (counterclockwise) inward from outside (or in an opposite direction), and the second spiral conductor 1208 winds counterclockwise (clockwise) inward from outside (or in an opposite direction).

Like the arrangement of FIG. 10, the two linear conductors have spiral shapes in opposite directions. Hence, when these linear conductors overlap, currents basically flow in the same direction at portions of the two spiral structures, and magnetic fields formed by the currents also have the same direction. For this reason, the magnetic fields have the effect of enhancing each other, and the reactance component is efficiently increased.

Circuit calculation and analysis were conducted for the electromagnetic band gap element according to this embodiment. The outline of dimensions used in the circuit calculation and analysis concerning the electromagnetic band gap element according to this embodiment is almost the same as in FIG. 6, and a description thereof will be omitted. As in FIG. 6, in the following circuit calculation and analysis, the unit cell size was set to 2.1 mm×2.1 mm, and the size of the conductor patch of the surface layer was set to 2.0 mm×2.0 mm. An FR-4 board having a 3-layer structure was used as the board in which standard numerical values were used as the board thickness, the distances between the layers, and the like, and a description thereof will be omitted here.

FIG. 15 is a graph showing the dispersion characteristic of the unit cell of the electromagnetic band gap element according to this embodiment. As is apparent from FIG. 15, the electromagnetic band gap element according to this embodiment has a band gap characteristic representing that the phase constant is 0 in a frequency band of 1.1 GHz or more. That is, in the electromagnetic band gap element according to this embodiment, the interior of the conductor patch of the surface layer is hollowed out, and the first linear conductor is formed on the same plane as the conductor patch to form a three-layer structure. Even with this arrangement, it is possible reduce the size of the element and increase the degree of freedom in the design, as in the first embodiment.

An example of target frequency adjustment in the arrangement of the electromagnetic band gap element according to this embodiment will be described next. In this case, the target frequency is set to 2.4, and the number of windings of the first spiral conductor 1207 formed on the surface layer in FIG. 12 and that of the second spiral conductor 1208 formed in the inner layer are deceased by one to further reduce the size.

Figure 16:
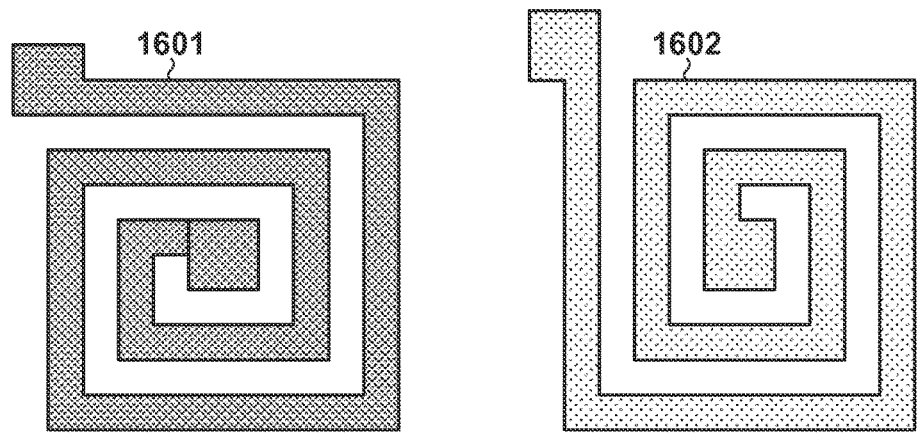
FIG. 16 is a plan view showing another example of the arrangement of conductors formed in the surface layer and the inner layer of the electromagnetic band gap element according to the second embodiment.

FIG. 16 illustrates linear conductors 1601 and 1602 used in place of the spiral conductors 1207 and 1208. The first linear conductor 1601 is formed on the same plane as the plane where the conductor patch 1201 is formed, like the first spiral conductor 1207 shown in FIG. 12. The second linear conductor 1602 is formed on the plane (inner layer) located between the planes where the conductor patch 1201 and the ground conductor 1202 are formed, respectively, like the second spiral conductor 1208 shown in FIG. 12. As shown in FIG. 16, the two conductors have spiral shapes in directions opposite to each other. Note that in this example as well, one end of the first linear conductor 1601 is connected to the conductor patch at a node, and the other end is connected to one end of the second linear conductor 1602 by a via. Similarly, the one end of the second linear conductor 1602 is connected to the first linear conductor 1601 by a via, and the other end is connected to the ground conductor by a via.

As in FIGS. 10 and 14, the two linear conductors having spiral shapes in opposite directions overlap. Hence, currents basically flow in the same direction at portions of the two spiral shapes, and magnetic fields formed by the currents also have the same direction. For this reason, the magnetic fields have the effect of enhancing each other, and the reactance component is efficiently increased.

Figure 17:
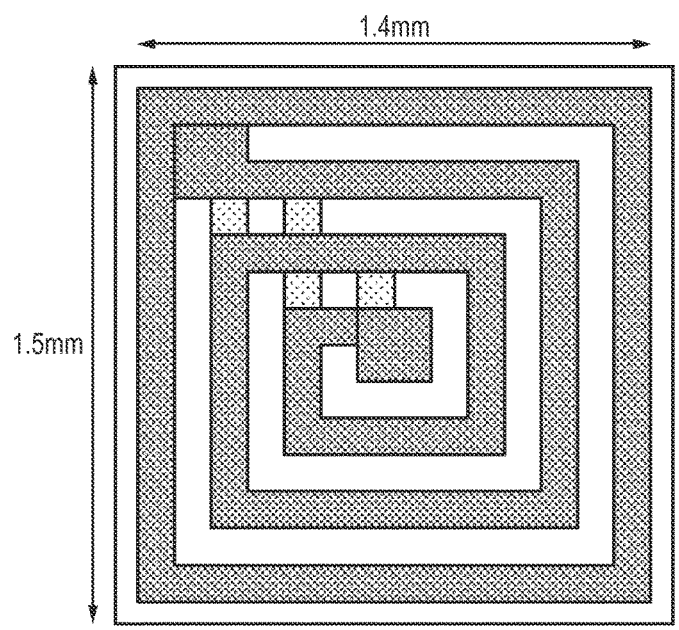
FIG. 17 is a view showing an example of the dimensions of the electromagnetic band gap element shown in FIG. 16.

FIG. 17 shows the outline of dimensions used in circuit calculation and analysis of the electromagnetic band gap element according to this embodiment. As shown in FIG. 17, the unit cell size was set to 1.5 mm×1.5 mm, and the size of the conductor patch of the surface layer was set to 1.4 mm×1.4 mm. An FR-4 board having a 3-layer structure was used in which standard numerical values were used as the board thickness, the distances between the layers, and the like, and a description thereof will be omitted here.

Figure 18:
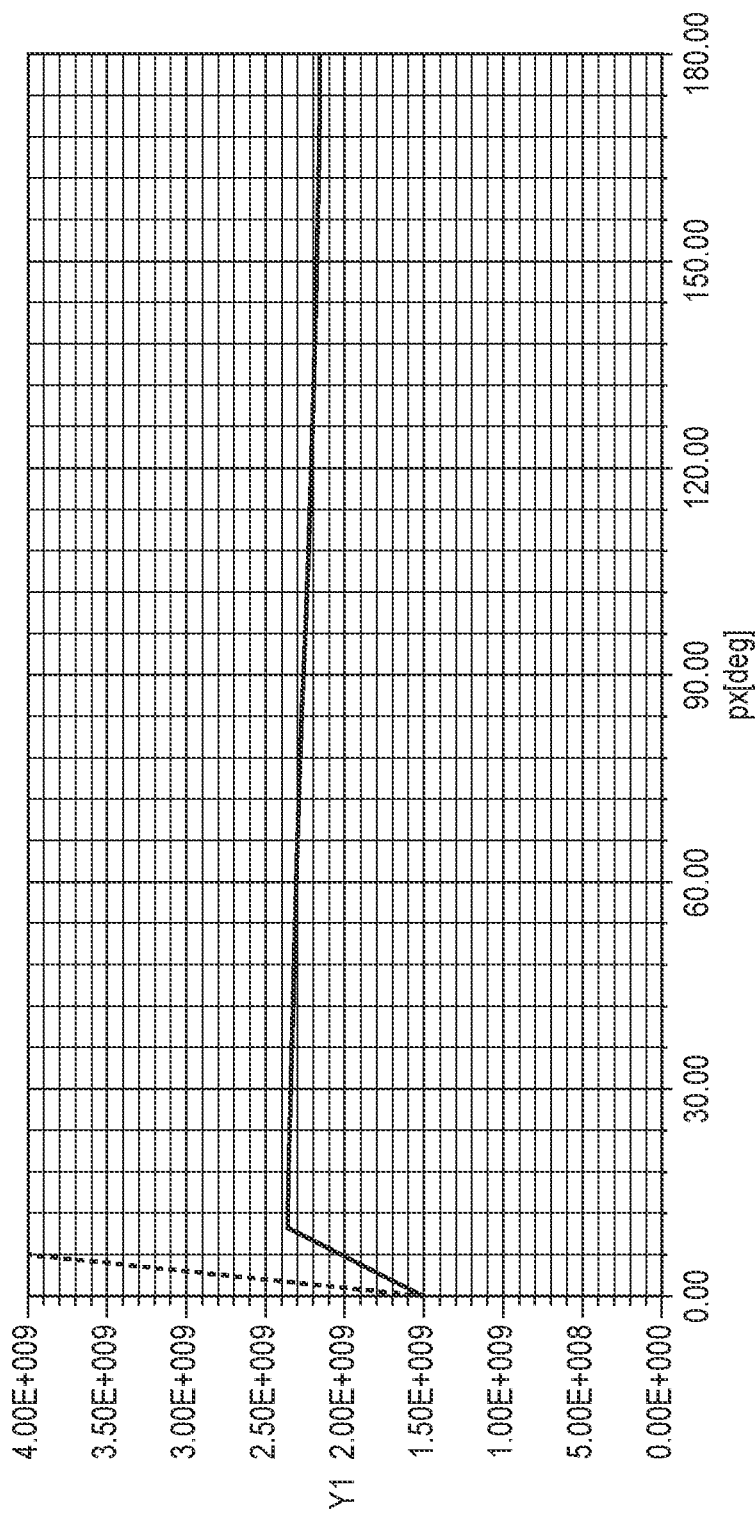
FIG. 18 is a graph showing the dispersion characteristic of the unit cell of an electromagnetic band gap element having the conductor arrangement shown in FIG. 16 in the inner layer.

FIG. 18 is a graph showing the dispersion characteristic of the unit cell of an electromagnetic band gap element having the linear conductors shown in FIG. 16. As is apparent from FIG. 18, the electromagnetic band gap element having the linear conductors shown in FIG. 16 has a band gap characteristic representing that the phase constant is 0 in a frequency band of 2.4 GHz or more. As can be seen, the band gap frequency is lower in the electromagnetic band gap element having the linear conductors shown in FIG. 16, as compared to the dispersion characteristic of the electromagnetic band gap element having only one layer of a spiral conductor shown in FIG. 8. That is, it was found that the band gap frequency can lower even when the unit cell size is reduced to about ¾ by the electromagnetic band gap element having the linear conductors shown in FIG. 16.

As described above, using spiral linear conductors having a multilayered structure makes it possible to lower the band gap frequency while keeping the unit cell forming the electromagnetic band gap structure in the same size as the conventional structure or implement the same band gap frequency using a smaller cell structure.

Note that in FIGS. 10, 14, and 16, the linear conductors formed in the respective layers have the same line width and conductor spacing. However, the present invention is not limited to this. For example, even when the spirals of the first and second layers have different line widths, the same effects as described above can be obtained if the currents flow in the same direction concerning the spiral structures overlapping between the layers. In addition, the conductor spacing is not limited to a predetermined value. For example, the conductor spacing may be increased toward the center.

When forming a multilayered structure of spiral conductor portions, a two-layer structure is formed. However, the present invention is not limited to this. A multilayered structure including three or more layers can also be implemented by forming the connection structure of the spiral conductors of the respective layers such that the currents flow in the same direction at the overlapping portions. More specifically, when forming three or more layers of spiral conductors, the spiral conductors of the respective layers are formed such that the spirals are alternately directed in opposite directions when viewed from the upper or lower side. That is, for example, a conductor having a clockwise spiral shape is formed on the nth plane, and a conductor having a counterclockwise spiral shape is formed on the (n+1)th plane. The respective linear conductors are formed so as to overlap each other when viewed from a direction perpendicular to the planes to form them. This makes it possible to cause the currents to flow in the same direction in the respective layers.

Various conductor shapes as shown in FIGS. 9A to 9E are applicable as the linear conductors, as in the above-described examples. That is, any conductors such as those having a serpentine shape as shown in FIGS. 9A to 9E can be formed as long as they are configured to overlap at least in part when viewed from a direction perpendicular to the planes where the linear conductors are formed, and the currents flow in the same direction in the overlapping part.

Note that the above electromagnetic band gap element has been explained concerning one unit cell. The unit cells are one- or two-dimensionally arrayed, thereby constituting one electronic circuit that implements the electromagnetic band gap element.

According to the present invention, it is possible to make an electromagnetic band gap structure compact.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-171709 filed on Aug. 21, 2013, which is hereby incorporated by reference herein in its entirety.

What is claimed is:

1. An electromagnetic band gap element comprising:
   a first planar conductor and a second planar conductor respectively formed on a first plane and a second plane which are parallel to each other and having a space between them, wherein the first planar conductor and second planar conductor are directly above and below each other; and
   at least two first linear conductors respectively formed on at least two third planes that are parallel to the first plane and the second plane and are located between the first plane and the second plane, wherein two first linear conductors out of the at least two first linear conductors are formed such that the two first linear conductors overlap at least in part when viewed from a direction perpendicular to the first plane, and currents have the same direction in the part, and
   wherein one linear conductor is formed by connecting the at least two first linear conductors to each other at ends, and the first planar conductor and the second planar conductor are connected via the one linear conductor,
   wherein the phase constant is 0 in at least part of the frequency band, and wherein the frequency band is determined based on the at least two first linear conductors and the one linear conductor.

2. The element according to claim 1, wherein the first linear conductor has a spiral shape at least in part.

3. The element according to claim 1, wherein the first linear conductor has a serpentine shape at least in part.

4. An electromagnetic band gap element comprising:
   a first planar conductor and a second planar conductor respectively formed on a first plane and a second plane which are parallel to each other and having a space between them, wherein the first planar conductor and second planar conductor are directly above and below each other;
   a first linear conductor formed on at least one third plane that is parallel to the first plane and the second plane and is located between the first plane and the second plane; and
   a second linear conductor formed on the first plane, wherein
   the second linear conductor is connected to the first planar conductor at one end and to the first linear conductor at the other end, and the first linear conductor is connected to the second planar conductor, thereby connecting the first planar conductor and the second planar conductor via the first linear conductor,
   wherein the phase constant is 0 in at least part of the frequency band, and wherein the frequency band is determined based on the at least two first linear conductors and the one linear conductor.

5. The element according to claim 4, wherein the first linear conductor and the second linear conductor are formed such that at least part of the first linear conductor and at least part of the second linear conductor overlap when viewed from a direction perpendicular to the first plane, and currents have the same direction in the part.

6. The element according to claim 5, wherein the second linear conductor has a spiral shape at least in part.

7. The element according to claim 5, wherein the second linear conductor has a serpentine shape at least in part.

8. An electronic circuit formed by one- or two-dimensionally arraying an electromagnetic band gap element, wherein the electromagnetic band gap element comprises:
   a first planar conductor and a second planar conductor respectively formed on a first plane and a second plane which are parallel to each other and having a space between them, wherein the first planar conductor and second planar conductor are directly above and below each other; and
   at least two first linear conductors respectively formed on at least two third planes that are parallel to the first plane and the second plane and are located between the first plane and the second plane, wherein two first linear conductors out of the at least two first linear conductors are formed such that the two first linear conductors overlap at least in part when viewed from a direction perpendicular to the first plane, and currents have the same direction in the part, and
   wherein one linear conductor is formed by connecting the at least two first linear conductors to each other at ends, and the first planar conductor and the second planar conductor are connected via the one linear conductor,
   wherein the phase constant is 0 in at least part of the frequency band, and wherein the frequency band is determined based on the at least two first linear conductors and the one linear conductor.

9. An electronic circuit formed by one- or two-dimensionally arraying an electromagnetic band gap element, wherein the electromagnetic band gap element comprises:
   a first planar conductor and a second planar conductor respectively formed on a first plane and a second plane which are parallel to each other and having a space between them, wherein the first planar conductor and second planar conductor are directly above and below each other;
   a first linear conductor formed on at least one third plane that is parallel to the first plane and the second plane and is located between the first plane and the second plane; and
   a second linear conductor formed on the first plane,
   wherein the second linear conductor is connected to the first planar conductor at one end and to the first linear conductor at the other end, and the first linear conductor is connected to the second planar conductor, thereby connecting the first planar conductor and the second planar conductor via the first linear conductor,
   wherein the phase constant is 0 in at least part of the frequency band, and wherein the frequency band is determined based on the at least two first linear conductors and the one linear conductor.

10. An electromagnetic band gap element according to claim 1,
   wherein the electromagnetic band gap element has a band gap characteristic representing that the phase constant is 0 within the range of a frequency band from 2.0GHz to 3.3 GHz.

* * * * *